(12) United States Patent
Iwata

(10) Patent No.: US 10,551,377 B2
(45) Date of Patent: Feb. 4, 2020

(54) QUANTIFICATION METHOD OF AUTOANTIBODY

(71) Applicant: MagArray, Inc., Milpitas, CA (US)

(72) Inventor: Hideyuki Iwata, Kariya (JP)

(73) Assignee: MagArray, Inc., Milpitas, CA (US)

( * ) Notice: Subject to any disclaimer, the term of this patent is extended or adjusted under 35 U.S.C. 154(b) by 35 days.

(21) Appl. No.: 16/026,905

(22) Filed: Jul. 3, 2018

(65) Prior Publication Data

US 2019/0018011 A1    Jan. 17, 2019

Related U.S. Application Data

(60) Provisional application No. 62/532,225, filed on Jul. 13, 2017.

(51) Int. Cl.
| | | |
|---|---|---|
| G01N 33/531 | (2006.01) | |
| G01N 33/564 | (2006.01) | |
| G01N 33/543 | (2006.01) | |
| G01N 33/53 | (2006.01) | |

(52) U.S. Cl.
CPC ....... *G01N 33/564* (2013.01); *G01N 33/5306* (2013.01); *G01N 33/5434* (2013.01); *G01N 33/54333* (2013.01)

(58) Field of Classification Search
None
See application file for complete search history.

(56) References Cited

U.S. PATENT DOCUMENTS

| | | | | |
|---|---|---|---|---|
| 5,501,955 A * | 3/1996 | Bergman | ......... | G01N 33/54306 435/28 |
| 6,933,364 B1 * | 8/2005 | Hattori | ................. | C07K 14/723 435/69.1 |
| 2008/0166738 A1 * | 7/2008 | Norman | ........... | G01N 33/57438 435/7.1 |
| 2013/0273579 A1 * | 10/2013 | Sawasaki | ............. | G01N 33/564 435/7.92 |
| 2015/0377893 A1 | 12/2015 | Osterfeld et al. | | |
| 2017/0176432 A1 | 6/2017 | Arase et al. | | |

OTHER PUBLICATIONS

Hartmann et al., Expanding Assay Dynamics: A Combined Competitive and Direct Assay System for the Quantification of Proteins in Multiplexed Immunoassays, Clinical Chemistry, 54:6, 2008, pp. 956-963. (Year: 2008).*

Strassman et al., Autoantibodies Against Glucuronosyltransferases Differ Between Viral Hepatitiis and Autoimmune Hepatitis, Gastroenterology 111, 1996, pp. 1576-1586. (Year: 1996).*

Braitbard et al. (2006) "Competition between bound and free peptides in an ELISA-based procedure that assays peptides derived from protein digests," Proteome Science, BioMed Central: 4(12): 1-14.

\* cited by examiner

*Primary Examiner* — Gary Counts
(74) *Attorney, Agent, or Firm* — Rudy J. Ng; Bozicevic, Field & Francis LLP

(57) ABSTRACT

A method of quantifying an autoantibody includes the steps of reacting a biological sample containing the autoantibody as a test substance with an antigen that is specifically recognized by and bound to the autoantibody, in competition with a known amount of a competition antibody that competes with the autoantibody for binding to the antigen; reacting the autoantibody bound to the antigen with a detection antibody that recognizes and binds to the autoantibody, but does not recognize the competition antibody; measuring a signal derived from the detection antibody bound to the autoantibody; and calculating an amount of the autoantibody contained in the biological sample by utilizing, as an index therefor, an amount of the competition antibody that provides 50% reduction of the signal derived from the detection antibody which is bound to the autoantibody in absence of the competition antibody.

3 Claims, 3 Drawing Sheets

QUANTIFICATION METHOD OF AUTOANTIBODY

TECHNICAL FIELD

This disclosure relates to a quantification method of autoantibody.

INTRODUCTION

In a living body, immune tolerance is established under a physiological state, so that no overresponse is elicited to a self-component such as self-normal cells or tissues, etc. However, if immune tolerance collapses due to a certain cause, the immune system becomes unable to discriminate self from non-self-component and produces an autoantibody, which is an antibody against the self-component. Autoantibody is implicated in autoimmune diseases that cause disorder in a specific organ disorder or systemic disorder. Therefore, an autoantibody that appears in high frequency in a particular disease is considered as being of significance in implementing diagnosis of an autoimmune disease. It is also known that an autoantibody accompanies certain cancers. So, its clinical utility is suggested, such as use thereof as a cancer marker for early diagnosis of cancer.

In general, in quantifying a test substance contained in a biological sample, a reagent called a high-purity standard substance is employed. According to a general practice, some standard samples containing such standard substance at different known amounts are prepared. Then, based on a calibration curve indicative of relation between measured values of signal intensities obtained from these standard samples and the amounts of standard substance contained respectively therein, the amount of the test substance contained in the respective biological samples is quantified from measured values obtained when actual biological samples as test specimen are used.

For instance, a method is reported in which an autoantibody purified from a patient specimen is employed as a standard substance in quantification of the autoantibody (see Reference 1 (J. Sheldon, et al., "Strategies for building reference standards of autoantibodies, Frontiers in immunology", Volume 6, Article 194)). This method employs purified autoantibody contained in the biological samples. However, the autoantibody purification requires a highly technical and complex technique, thus being troublesome and costly. Moreover, a great amount of patient specimen is required for obtaining a required amount of autoantibody as the standard substance. Including such situation as above, in quantification of an autoantibody, it is difficult to purchase/obtain a standard substance of high purity, and accurate quantification of autoantibody contained in a biological sample is difficult also. In particular, in recent years, there has been a need for multiplex simultaneous analysis of a plurality of kinds of autoantibody amounts. However, since it is difficult to purify a plurality of kinds of autoantibody and to provide them as standard substances as described above, it is believed that the method utilizing purified autoantibody disclosed in Reference 1 is not suitable for use in the multiplex simultaneous analysis.

Further, Reference 1 discloses also a method of using a patient's blood sample per se as a substitute for a standard substance. This method disclosed in Reference 1 has an advantage that it does not require such troublesome technique as purification for utilization of the patient's blood sample and it allows easy and inexpensive preparation of standard substance substitute. However, since the absolute amount of autoantibody contained in the standard substance substitute is unknown, the method comprises merely semi-quantification due to inability of evaluation based on an absolute amount. Further, if the lot of the patient's sample is changed, this may result in variation in the determined value. Thus, in order to compensate for such inter-lot difference, the method requires a separate operation comprising e.g. concentration adjustment so as to be able to obtain a same signal when the lot is changed. This is another problem with the above method.

Further, for determination of autoantibody, there is also reported a method of determining a plurality of autoantibodies that allows multiplexed analysis of a small amount of samples with using a technique called "Luminex" (a registered trademark), in which a substance bonding with a test substance is individually fixed to microbeads stained with two colors of florescent dye in various concentrations in combination (see Reference 2 (V. Doseeva, et al., "Performance of a multiplexed dual analyte immunoassay for the early detection of non-small cell lung cancer", Journal of Translational Medicine, 13:55, (2015)). In view of the difficulty of preparing purified products of a plurality of autoantibodies as standard substances, in the method disclosed in Reference 2, no calibration curve is produced; instead, based on values obtained by subtracting blind test values from actually determined values, determination of autoantibodies as test substances is affected. Therefore, this method provides the advantage of not requiring such troublesome technique of autoantibody purification, preparation of calibration curve, etc. and allowing easy and inexpensive determination. However, like the method disclosed in Reference 1 using blood sample per se as a standard substance substitute, the above method too suffers the problem of being merely a semi-quantification due to the absolute amount of the autoantibody being unknown. Moreover, since there exists dispersion among determined values of titer of a reagent used in the determination, it is anticipated that determined value will vary at the time of lot change of determination reagent. Therefore, this method suffers another problem of requiring strict control of determination reagent and difficulty of obtaining stable determined value.

Further, determination of autoantibody is possible also based on competitive inhibition to an antigen immobilized on a solid phase. In this, in general, it is necessary to employ a highly purified antigen as the antigen and to immobilize this on the solid phase. In contrast, it is reported that if an antibody capturing the antigen (capture antibody) is immobilized on a solid phase surface, an antigen molecule can be selectively presented on the solid phase surface even in the case of a crude antigen, such as a low purity antigen in the form of an organ extract (see Reference 3 (Japanese Patent No. 2675676). In this way, Reference 3 describes that an autoantibody contained in a patient's sample can be determined even when a low-purity antigen is employed. Yet, there remains room for improvement in determination of an absolute amount of autoantibody.

As described above, the convention has not yet reported any method that has both readiness and quantitativity in determination of an autoantibody amount in a biological sample. The convention effects the determination with placing focus only on either one of readiness and quantitativity. Further, in recent years, there has been a need to devise a technique that realizes a multiplex simultaneous analysis capable of determining amounts of a plurality of kinds of autoantibody at one time.

SUMMARY

Thus, a need exists for a quantification method of autoantibodies which is not susceptible to the drawbacks described above.

According to one aspect of the present invention, there is provided a method of quantifying an autoantibody comprising the steps of:

reacting a biological sample containing the autoantibody as a test substance with an antigen that is specifically recognized by and bound to the autoantibody, in competition with a known amount of a competition antibody that competes with the autoantibody for binding to the antigen;

reacting the autoantibody bound to the antigen with a detection antibody that recognizes and binds to the autoantibody, but does not recognize the competition antibody;

measuring a signal derived from the detection antibody bound to the autoantibody; and calculating an amount of the autoantibody contained in the biological sample by utilizing, as an index therefor, an amount of the competition antibody that provides 50% reduction of the signal derived from the detection antibody which is bound to the autoantibody in absence of the competition antibody.

BRIEF DESCRIPTION OF DRAWINGS

The foregoing and additional features and characteristics of this disclosure will become more apparent from the following detailed description considered with the reference to the accompanying drawings, wherein.

DETAILED DESCRIPTION

Figure 1:
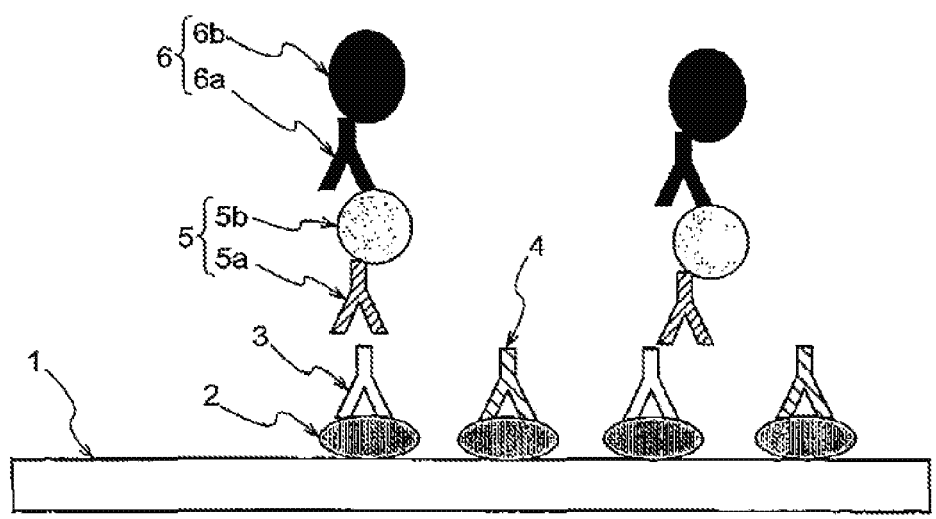
FIG. 1 is a diagram showing one mode of a principle of autoantibody quantification method relating to this disclosure, showing a mode utilizing a solid phase technique.

A quantification method of autoantibody according to an embodiment disclosed here will be explained with reference to the accompanying drawings.

The quantification method of autoantibody according to this disclosure is configured to determine an amount (a concentration) of an autoantibody contained as a test substance in a biological sample in the form of an absolute value. In the determination, the method utilizes an antibody (may sometimes be referred to as a "competition antibody" hereinafter) that competes with the autoantibody for binding to an antigen that is specifically recognized by and bound to the autoantibody. The competitive antibody, in various known amounts (concentrations), is added to the biological sample for reaction of binding to the antigen in competition with the autoantibody (may sometimes be referred to as a "competitive reaction" hereinafter). In this, the autoantibody that binds to the antigen decreases with increase of the amount of the competitive antibody added. It increases with decrease of the amount of the competitive antibody. The method calculates the amount of autoantibody contained in the biological sample based on reduction in a binding ratio of the autoantibody relative to the antigen and on an amount of competitive antibody added. The existence of the competitive antibody reduces the binding ratio of the autoantibody and the antigen. The amount of autoantibody is calculated by comparing the reduction rate of the binding ratio and the amount of competitive antibody.

In the quantification method of autoantibodies according to this disclosure, the autoantibody as the test substance is not particularly limited, but can be any antibody which recognizes a self body constituent component in a living body as an "antigen" (autoantigen). Therefore, it can be an autoantibody specific for one particular organ whose antigen is limited to such one organ or can also be an antigen widely distributed in a living body such as a non-organ specific autoantibody, e.g. an anti-nuclear antibody acting to a nuclear component of a cell as an autoantigen. For instance, an autoimmune disease is known wherein an autoantibody for a particular body constituent component is produced due to collapse of immune tolerance, thus leading to a particular pathological condition. The autoantibody that caused the particular pathological condition can preferably be used as a test substance to be subjected to the quantification. Other preferred but not-limiting examples of the test substance include autoantibodies that act to a protein as an antigen that is specifically expressed in a particular pathological condition such as a cancer, thus acting as a cancer marker or a protein that is overexpressed in a particular pathological condition such as a cancer, etc. For example, autoantibodies for a protein specifically or overly produced in a cancer cell can be cited. Also, it is known that a cancer develops when an abnormality occurs in a cancer regulatory gene relating to control of gene repair, cell cycle, thus mutation and eventual dysfunction of a protein coding for such cancer regulatory gene. It is known that in the above process, an autoantibody for such mutant protein is produced. Such autoantibody is another preferred example of the test substance.

The autoantibody can be an autoantibody implicated in an autoimmune disease. As examples thereof, there can be cited anti-nuclear antibodies including an anti-dsDNA antibody, an anti-ssDNA antibody, an anti-histone antibody, an anti-RNA antibody, an anti-RNP antibody, an anti-Sm antibody, an anti-SS-A antibody, an anti-SS-B antibody, an anti-Scl-70 antibody, an anti-PCNA antibody, an anti-ribosome antibody, an anti-mitochondria antibody, an anti-centromere antibody, an anti-IgG antibody such as a rheumatoid factor, an anti-thyroglobulin antibody, an anti-thyroid peroxidase antibody, an anti-microsome antibody, an anti-acetylcholine receptor antibody, an anti-erythrocycle antibody, an anti-platelet autoantibody, an anti-glomerular basement antibody, an anti-Langerhans islet antibody, an anti-adrenocortical cell antibody, an anti-gastric parietal cell antibody, etc. But, the autoantibody is not limited to these.

Further, the autoantibody can be an autoantibody implicated in a cancer. For instance, it can be an autoantibody for a tumor associated antigen (TAA) for a protein whose genetic mutation induces canceration, such as a protein specifically expressed in a cancer cell, a protein overexpressed in a cancer cell, a cancer suppressing protein, etc. As some non-limiting examples thereof, NY-ES0-1, c-Myc, HER2, CEA, MUC1, PSMA, Survivin, livin, EGFR, CA19.9, PAI-1, MDM2, cyclin B1, Imp1, Koc, NPM1, p53, p16, etc. Moreover, the autoantibody can be an autoantibody for a protein associated with maintenance of biofunction of metabolic system, angiogenesis, etc. For example, autoantibodies for ANGPTLs, such as Angiopoietin-Like Protein 3 (may be referred to also as "ANGPTL3" in short hereinafter). However, the autoantibody is not limited to the above.

The source of the autoantibody too is not particularly limited. As examples of thereof, animals such as a human, non-human primate, a rabbit, a rat, a guinea pig, a mouse, a dog, a cat, a horse, bovine, a pig, a sheep, a goat, a fowl can be cited, but a human is particularly preferred. Therefore, the quantification method of autoantibody according to this disclosure preferably employs an autoantibody contained in a human-derived biological sample as a test substance.

In the quantification method of autoantibody according to this disclosure, the biological sample containing an autoantibody as a test substance is not particular limited, but can be any such sample that can contain an autoantibody as a test substance subjected to the quantification. As some non-limiting examples thereof, body fluids derived from a living body such as blood, plasma, serum, cerebral spinal fluid, amniotic fluid, milk, sweat, urine, saliva, sputum, feces, tissue, cell culture from an animal, etc. can be cited. Particularly preferred example is a human-derived biological sample, more preferably, a patient specimen sampled from an affected or possibly affected patient. Such biological sample, if necessary, can be subject to a preliminary treatment such as isolation, purification, concentration, etc. Therefore, the biological sample can comprise a body fluid sampled from a living body added, if necessary, with other component such as a diluent, a preservative, a stabilizer, a buffer, etc.

The autoantibody quantifying method of this disclosure, preferably comprises the following steps.

(i) reacting a biological sample containing the autoantibody as a test substance with an antigen that is specifically recognized by and bound to the autoantibody, in competition with a known amount of a competition antibody that competes with the autoantibody for binding to the antigen (step of reacting with competition antibody);

(ii) reacting the autoantibody bound to the antigen with a detection antibody that recognizes and binds to the autoantibody, but does not recognize the competition antibody (step of reacting with detection antibody);

(iii) measuring a signal derived from the detection antibody bound to the autoantibody (step of measuring signal derived from detection antibody); and (iv) calculating an amount of the autoantibody contained in the biological sample by utilizing, as an index therefor, an amount of the competition antibody that provides 50% reduction of the signal derived from the detection antibody which is bound to the autoantibody in absence of the competition antibody (step of calculating autoantibody amount).

Next, the above respective steps (i) through (iv) will be described in details. It is understood, however that the autoantibody quantifying method of this disclosure is not limited thereto, but various modifications are possible when appropriate or needed.

(i) Step of Reacting with Competition Antibody:

In the autoantibody quantifying method of this disclosure, at step (i) a biological sample containing the autoantibody as a test substance is reacted with an antigen that is specifically recognized by and bound to the autoantibody, in competition with a known amount of a competition antibody that competes with the autoantibody for binding to the antigen. With this, the autoantibody and the competition antibody are competitively bound to the antigen.

The antigen for use in the autoantibody quantifying method of this disclosure can be appropriately selected, depending on the kind of the autoantibody as the test substance. Any substance can be used that can bind specifically to the autoantibody as the test substance to form an antigen-antibody complex (an immune complex). Preferably, the antigen is a substance containing an epitope that has a structure complimentary to a complementarity determining region of a variable region or a super variable region of the autoantibody as the test substance. For instance, a protein, a polypeptide, a peptidemimetic, a peptide nucleic acid, a polysaccharide, a glycoprotein, etc. can be the antigen. The antigen can be an antigen isolated and purified form the biological sample or an antigen prepared by a genetic recombination technique or a chemical synthesis technique or can even be a commercially available product. For instance, if the sequence information of the antigen is known, an expression vector can be prepared by incorporating a DNA fragment synthesized based on such sequence information into an appropriate vector. Then, with using this expression vector, an appropriate host of e.g., a cell of a microorganism (*E. coli*, yeast), an insect, an animal, is transformed to express a protein, which protein can be used as the antigen. Further, the polypeptide can be prepared by chemical or enzymatic cleavage of the protein and such too can be used as long as it retains the above-described epitope.

The amount of antigen will be appropriately set in accordance with an estimated amount of autoantibody contained in the biological sample, a methodology of determining the signal derived from the autoantibody via the detection antibody, etc. Preferably, the amount can sufficiently react with the estimated amount of autoantibody contained in the biological sample. For instance, the amount of antigen can be from 1 pg to 10 μg, preferably from 10 pg to 1 μg.

The antigen, when necessary, can be immobilized on an insoluble support (solid support). As such solid support, e.g. a synthetic polymer substance such as polystyrene, polyethylene, polypropylene, an insoluble polysaccharide such as agarose, dextran, polysaccharide, or an inorganic substance such as glass, silica gel, bentonite, can be used preferably. And, these supports can be used in a form of a sensor element, a microplate. A membrane, a test tube, etc. or can be in a form of a sphere, a bar, a micro particle (bead), etc.

The immobilization to the solid support can be carried out conventionally. Any conventional technique can be employed as long as it allows stabilization of the immobilized antigen and maintenance of its function and it does not cause direct binding of the autoantibody contained in the biological sample, the competition antibody, the detection antibody, etc. to be added subsequently to the reaction to the solid support, bypassing the antigen. As some examples of the immobilization, the physical adsorption technique, the chemical bonding technique, etc. can be cited. The physical adsorption technique can be implemented by causing the antigen into contact with the solid support in an aqueous solvent such as water, physiological saline solution, various buffer solutions. As some examples of the chemical binding technique, immobilization through formation of covalent bond, by diazo method, acid azide method, isocyanate method, cyanogen bromide method can be cited. Further, it is also possible to employ an immobilization method using a cross-linking agent such as a multifunctional reagent having two or more functional groups of glutaraldehyde, etc. For stable immobilization of the antigen as a protein, a highly reactive functional group can be introduced by chemical modification of the solid support surface. 3-aminopropyltriethoxysilane For instance, by forming a thin layer of (3-APTES), polyethyleneimine (PEI), ethylenediamine, etc. on the surface of solid support, a functional group of an amino group or the like can be introduced. Immobilization is also possible via a reactive side chain (spacer) having an appropriate chain length, biotin-avidin (streptavidin) binding, a protein such as an albumin, protein A, etc. Further, immobilization is also possible with using an antibody that specifically recognizes and binds to an antigen, like the so-called sandwich method.

In the immobilization, in order to suppress direct binding to the solid support by the autoantibody in the biological sample, the competition antibody and the detection antibody to be subsequently added to the reaction system, a treatment of the solid support surface, such as blocking, can be effected if necessary.

The competition antibody for use in the quantification method of autoantibody relating to this disclosure can be any substance that competes with the autoantibody for binding to the antigen which is the binding partner of the autoantibody as the test substance. Here, the term "competition" means ability to provide detectable reduction in the antigen-antibody reaction between the autoantibody as the test substance and the antigen as its binding partner in the autoantibody quantification method of this disclosure. Therefore, the competition antibody recognizes and binds to the antigen specifically recognized and bound by the autoantibody as the test substance, just like the autoantibody. Preferably, the competition antibody recognizes an identical or substantially identical epitope as the autoantibody of the test substance. With this, the competition antibody inhibits binding of the autoantibody to the corresponding antigen, in particular, to the epitope of the antigen, so that binding of one antigen molecule results in inability of the binding of the autoantibody to this antigen molecule, or conversely, binding of the competition antigen to one antigen molecule results in inability of binding of this competition antibody to the antigen molecule. Therefore, the amount of autoantibody binding to the antigen decreases with increase of the amount of competition antibody added or increases with decrease of the amount of competition antibody added. The degree of such decrease in the antigen-antibody reaction can be determined by any method known in the art to which this disclosure pertains. For instance, such degree determination can be effected by comparison of binding activity obtained in a control test which is affected in the absence of the candidate competition antibody. Preferably, the competition antibody has a same apparent affinity level as the autoantibody as the test substance. For instance, it is preferred that an apparent equilibrium dissociation constant ($K_d$ value) of the autoantibody exhibit a same digit of $K_d$ value of the competition antibody. Here, $K_d$ value represents the affinity of the antibody, which is a concentration ratio between reactants (antibody (Ab) and antigen (Ag)) and the reaction product (antigen-antibody complex (Ag-Ab)) when the binding reaction generated by mixture of the antigen and the antibody at certain mol concentrations reaches an equilibrium and this can be calculated as $K_d=[Ag]\times[Ab]/[Ag-Ab]$. The concentrations of the antibody, the antigen and the antigen-antibody concentration under equilibrium can be obtained by using e.g. equilibrium dialysis method, surface plasmon resonance method, etc.

Preferably, the competition antibody does not recognize or bind to the detection antibody which is added at the subsequent step. That is, it has no cross-reactivity to the detection antibody. Further preferably, the competition antibodies themselves do not recognize or bind to each other or do not recognize or bind to the autoantibody, either.

The competition antibody can be either a polyclonal antibody or a monoclonal antibody, as long as it has the above-described characteristics. And, its origin is not particularly limited, either. Therefore, the competition antibody can be a commercially available product and also a polyclonal antibody obtained by immunization of an animal such as a mouse, a rat, a rabbit, a goat, a sheep, a guinea pig, with using, as an immunogen, a target antigen for the autoantibody as the test substance or a constituent component of a part of such target antigen. Incidentally, in the above, it is required that the language "a constituent component of a part of such target antigen' be inclusive of an epitope recognized by the autoantibody of the test substance. Especially preferably, an antibody obtained by immunization of an animal different from the origin of the autoantibody as the test substance can be employed. Moreover, an animal can be immunized with e.g. a synthetic peptide containing a single epitope of the constituents of the target antigen and a hybridoma cell can be obtained through cell fusion of an antibody-producing cell that produces an antibody that recognizes this epitope and a myeloma cell. Then, such hybridoma cell is cultured to produce a monoclonal antibody, which monoclonal antibody too can be used preferably. For instance, if the sequence information of the target antigen is known, an expression vector can be prepared by incorporating a DNA fragment synthesized based on such sequence information into an appropriate vector. Then, with using this expression vector, an appropriate host of e.g. a cell of a microorganism (E. coli, yeast), an insect, an animal, is transformed to express a protein, which protein then can be used as the antigen in immunization of an appropriate animal. In particular, preferably, a human-derived recombinant protein is produced in a non-human host by the genetic engineering technique and a non-human animal is immunized with using such recombinant protein as the immunogen. In immunization, an appropriate adjuvant can be used in combination, when needed.

Moreover, the competition antibody can also be an antibody fragment such as F(ab')$_2$ fragment, Fab fragment, Fv fragment, retaining an antigen binding ability, which fragment can be obtained by treating a whole antibody with a proteolytic enzyme such as papain, pepsin, etc. The competition antibody can be one prepared by a known genetic engineering technique such as the genetic recombination and chemical synthetic technique. In the case of competition antibody preparation by genetic recombination, if the test substance is a human autoantibody, the competition antibody can be a chimeric antibody having domains other than the H-chain and L-chain variable regions substituted for by human corresponding domains or a humanized antibody in which a primary structure other than H-chain and L-chain complementarity determining regions substituted for by a corresponding primary structure of human antibody or a fully humanized antibody with substitution by a primary structure corresponding to a human antibody including the constant region.

In use of the competition antibody, a reaction solution is prepared by adding a known amount thereof to a biological sample containing an autoantibody as a test substance. Then, this reaction solution is placed in contact with an antigen, so that the competition antibody competes with the autoantibody in the biological sample for binding to the antigen. The timing of adding the competition antibody is not particularly limited. However, for allowing a presence ratio between the autoantibody and the competition antibody to be reflected in the competition reaction, it is preferred that the reaction with the antigen occur after addition of the competition antibody to the biological sample.

The competition antibody is to be added in various amounts. If the competition antibody amount is large, the ratio of the autoantibody to bind to the antigen is small. Conversely, if the competition antibody amount is small, the ratio of the autoantibody to bind to the antigen is large. The competition antibody should be added by an amount that allows determination of such phenomena as above. The specific addition amount is to be set appropriately in accordance with affinities of the competition antibody and the autoantibody to the antigen, the estimated amount of autoantibody contained in the biological sample, the method of determining signal derived from the autoantibody via the detection antibody, etc. For instance, the amount of competition antigen can be from 1 pg/ml to 1 mg/ml, preferably from 10 pg/ml to 1 µg/ml.

Preferably, the competition antigen is added to the biological sample in the form of a competition antigen solution obtained by solution or suspension thereof in an appropriate aqueous solution such as water, physiological saline solution, various buffer solutions, etc. The buffer solution can be any buffer solution known in the art. As examples thereof, phosphate buffer solution, citrate buffer solution, imidazole buffer solution, TRIS buffer solution, HEPES buffer solution, MOPS buffer solution, but it is not limited thereto.

The operational procedure, reaction condition, etc. in the reaction step with the competition antibody at step (i) can be implemented similarly to the standard immunoassay. In case the antigen is immobilized on the solid support, it is preferred that after the reaction, autoantibody and competition antibody un-reacted with the antigen be removed by washing with an appropriate aqueous solution such as water, physiological saline solution, various buffer solutions, etc.

(ii) Step of Reacting with Detection Antibody

In the autoantibody detection method of this disclosure, at step (ii), the autoantibody bound to the antigen is reacted with a detection antibody that recognizes and binds to the autoantibody, but does not recognize the competition antibody. With this, only the autoantibody bond to the antigen binds to the detection antibody, whereas this detection antibody does not bind to the competition antibody bound to the antigen, or to the autoantibody or competition antibody non-reacted with the antigen.

The detection antibody for use in the autoantibody quantification method of this disclosure can be any substance without limitations, as long as it recognizes and binds to the autoantibody as the test substance. Further, it is required that the detection antibody not recognize or bind to the competition antibody and not have cross-reactivity relative to the competition antibody. It is further preferred that detection antibodies themselves not recognize or bind to each other.

The detection antibody can be either a polyclonal antibody or a monoclonal antibody, as long as it has the above-described characteristics. And, its origin is not particularly limited, either. Therefore, the detection antibody can be a commercially available product, just like the competition antibody. When a commercially available product is employed, the detection antibody can be selected in accordance with the isotype (IgG, IgM, IgA, IgD, IgE) or subclass of the isotype of the autoantibody of the test substance. Isotypes are classified based on difference of antigenicity due to differences of constant region of the antibody. Many of the isotypes of the autoantibody contained in a biological sample derived from an animal such as a human are IgG. Thus, as the detection antibody, an antibody for IgG is selected preferably. For instance, the human IgG can be classified into tour subtypes of IgG1, IgG2, IgG3, IgG4, whereas the mouse antibody can be classified into IgG1, IgG2a, IgG2b, IgG3.

The detection antibody can be prepared, similarly to the competition antibody. A polyclonal antibody obtained by immunizing an animal such as a mouse, a rat, a rabbit, a goat, a sheep, a guinea pig, or the like with an autoantibody as a test substance or a constituent component of the autoantibody as an immunogen can be used preferably. Further, an animal can be immunized with e.g. a synthetic peptide containing a single epitope of the constituents of the autoantibody and a hybridoma cell can be obtained through cell fusion of an antibody-producing cell that produces an antibody that recognizes this epitope and a myeloma cell. Then, such hybridoma cell is cultured to produce a monoclonal antibody, which monoclonal antibody too can be used preferably. Incidentally, the constituent component of the autoantibody is used preferably with using a constant region of the autoantibody of the test substance, in particular the Fe fragment as an immunogen. In case the detection antibody recognizes the constant region of the autoantibody, it is preferred that the competition antibody have a different isotype or subtype. As for the immunization, an appropriate adjuvant can be used when necessary.

Moreover, the detection antibody can also be an antibody fragment such as $F(ab')_2$ fragment, Fab fragment, Fv fragment, retaining an antigen binding ability, which fragment can be obtained by treating a whole antibody with a proteolytic enzyme such as papain, pepsin, etc. The detection antibody can be one prepared by a known genetic engineering technique such as the genetic recombination, chemical synthetic technique. In the case of detection antibody preparation by genetic recombination, if the test substance is a human autoantibody, the detection antibody can be a chimeric antibody having domains other than the H-chain and L-chain variable regions substituted for by human corresponding domains or a humanized antibody in which a primary structure other than H-chain and L-chain complementarity determining regions substituted for by a corresponding primary structure of human antibody or a fully humanized antibody with substitution by a primary structure corresponding to a human antibody including the constant region.

The amount of detection antibody to be added is to be appropriately set in accordance with an estimated amount of the autoantibody contained in the biological sample, the method of determining a signal derived from the autoantibody via the detection antibody, etc. Preferably, it is an amount that allows sufficient reaction with the estimated amount of autoantibody contained in the biological sample. For instance, the amount of detection antigen can be a concentration from 0.01 to 100 µg/ml, preferably from 0.1 to 10 µg/ml.

Preferably, the detection antigen is added to the biological sample in the form of a detection antigen solution obtained by solution or suspension thereof in an appropriate aqueous solution such as water, physiological saline solution, various buffer solutions, etc. to the reaction solution after the competition reaction between the biological sample and the competition antibody to the antigen. The buffer solution can be any buffer solution known in the art. As examples thereof, phosphate buffer solution, citrate buffer solution, imidazole buffer solution, TRIS buffer solution, HEPES buffer solution, MOPS buffer solution, but it is not limited thereto.

The operational procedure, reaction condition, etc. in the reaction step with the detection antibody at step (ii) can be implemented similarly to the standard immunoassay. In case the antigen is immobilized on the solid support, it is preferred that after the reaction, detection antibody un-reacted with the antigen be removed by washing with an appropriate aqueous solution such as water, physiological saline solution, various buffer solutions, etc.

The detection antibody is directly and indirectly labelled with an appropriate labeling material As such labeling materials are known, one skilled in the art can select one for use appropriately. As long as stability and functionality are maintained, any known such material can be employed. As examples of labeling material, a magnetic substance, a radioactive substance, an enzyme, a fluorescent dye, a chemiluminescent material, etc. can be cited. And, one or a plurality of kinds thereof can be used. Therefore, the autoantibody quantification method of this disclosure can be implemented with using any known antigen-antibody reaction determination method including magnetic immunoassay, radioactive immunoassay (RIA, IRMA), enzyme immunoassay (EIA, ELISA), chemiluminescent immunoassay (CLIA), electric chemiluminescent immunoassay (ECLIA), and fluorescent enzyme immunoassay (FLEIA), etc.

The magnetic material (substance) as used herein means being inclusive of magnetic substance that is magnetized in a magnetic field. Magnetic substances are classified into ferromagnetic substance, diamagnetic substance, paramagnetic substance, superparamagnetic substance, ferrimagnetic substance, etc. Any such substance can be employed as long as it does not impair the specific affinities of the autoantibody as the test substance and the antigen or antibodies used in the determination, and the function of any other reagent. As examples thereof, there can be cited a ferromagnetic metal such as iron, cobalt, nickel, gadolinium, alloys of the ferromagnetic metals such as iron-nickel, iron-cobalt, etc. alloys containing a ferromagnetic metal, oxides of ferromagnetic metal represented by magnetite ($Fe_3O_4$), maghemite ($\gamma$-$Fe_2O_3$) or various ferrites as intermediates thereof. In particular, it is preferred to use ferrites from the viewpoint of chemical stability and reactivity to magnetic field. And, mixture of ferrite added with a metal such as cobalt, manganese, zinc, etc. can be used advantageously.

The shape and the size of the magnetic substance is not particularly limited. Any appropriate and advantageous shape and size can be selected. As examples of shape, shapes of sphere, ellipsoid, particle, cube, column, bar, plate, needle, fiber, lump, etc. can be cited. Preferably, the substance is formed into a uniform shape. Further, the magnetic substance can be prepared in the form of beads such as nano particles, micro particles.

The magnetic particle can be constituted solely of such magnetic substance or can be configured such that the magnetic substance is dispersed over the entirety of particles or surfaces thereof or can be incorporated within the particles. For instance, polymer prepared with the magnetic substance being uniformly dispersed therein may be prepared in the form of particles. Or, cores prepared with the magnetic material uniformly dispersed in polymer can be prepared with coating of the polymer. The polymer can be hydrophilic polymer or hydrophobic polymer and can be appropriately selected in accordance with a mode of determination. Specifically, a high molecular polymer such as polystyrene, silica gel, gelatin, polyacrylamide, etc. can be used advantageously. Further, the polymer can be configured to express its function with introduction of a functional group such as an amino group, a carboxyl group, a tosyl group, a hydroxyl group to the particle surface. Incidentally, preferably, the preparation should be effected such that the magnetization per particle be uniform.

As examples of appropriate radioactive substance, $^{32}P$, $^{35}S$, $^{131}I$, $^{45}Ca$, $^{3}H$, etc. can be cited. As examples of enzyme label, peroxidase, alkaline phosphatase can be cited. As examples of fluorescent dye, fluorescein isothiocyanate (FITC), tetramethylrhodamine (TAMRA), tetramethylrhodamine isothiocyanate (TRICA), Texas Red, cyanine dyes such as Cyanine 3 (Cy3), and Cyanine 5 (Cy5), quantum dot such as Qdot (registered trademark) can be cited. As examples of chemiluminescent substance, luminal, etc. can be cited. Further, digoxigenin or biotin can be used advantageously also. In case biotin is employed, reaction can be effected with using streptavidin labeled with e.g. HRP for a detection antibody labeled with biotin. In this, by affecting a plurality of biotin labeling on the detection antibody, the signal can be amplified so that sensitivity improvement is made possible. The labeling material is not limited to the above, any known substance can be used advantageously.

The labeling method of detection antibody can be any labeling method as long as it can maintain stability and function of the detection antibody and the labeling material and can also maintain the reaction stability of the autoantibody contained in the biological sample, the competition antibody and the antigen. For instance, as examples of labeling of detection antibody with magnetic particles, physical adsorption method, and chemical binding method can be cited. The physical adsorption method can be carried out by placing magnetic particles and detection antibody in an appropriate aqueous solution such as water, physiological saline solution, various kinds of buffer solutions. As some examples of the chemical binding technique, labeling method through formation of covalent bond, by diazo method, acid azide method, isocyanate method, cyanogen bromide method can be cited. Further, it is also possible to employ an immobilization method using a cross-linking agent such as a multifunctional reagent having two or more functional groups of glutaraldehyde, etc. And, as described above, a functional group such as an amino group, a carboxyl group, a tosyl group, a hydroxyl group, etc. introduced to the magnetic particle surface to express its function can be chemically bonded with a functional group on the detection antibody. Further, the magnetic particle and the detection antibody can be chemically bonded to each other via a reactive side chain having an appropriate chain length (a spacer) or a protein such as albumin, protein A, etc. Moreover, biotin-avidin (streptavidin) binding having high affinity and specificity or antigen-antibody reaction, etc. too can be employed.

The labeling of the detection antibody with a labeling material can be effected either before or after the formation of the immune complex of the detection antibody and the autoantibody as the test substance. Therefore, it is possible to arrange such that the autoantibody as the test substance is recognized and captured with using a detection antibody which was labeled with a labeling material in advance. Further, it is also possible to arrange such that the detection antibody is labeled with a labeling material after this detection antibody has recognized and captured the autoantibody.

(iii) Step of Measuring Signal Derived from Detection Antibody

In the autoantibody quantification method of this disclosure, the step (iii) is provided for measuring a signal derived from the detection antibody bound to the autoantibody. Such signal derived from the detection antibody is derived from the autoantibody boned to the antigen among autoantibodies contained in the biological sample. Therefore, the signal derived from the detection antibody is in direct proportion with the ratio of the autoantibody bound to the antigen.

The measurement of the intensity of the signal derived from the detection antibody can be effected by any conventional method. In case a label is added, the intensity can be measured by a known labeling detection method in accordance with the label used. For instance, in case the label is magnetic particle, it can be detected by a known magnetic detection method, preferably, by a magnetic sensor. The magnetic sensor is not particularly limited as long as it can detect a magnetic signal from the magnetic particle on the sensor surface. For instance, a Hall element, a magnetic (magneto-impedance: MI) element, a magnetic resistance element such as a magnetic resistance (Magneto Resistive: MR) element, a giant magneto resistive element, a tunnel magneto resistive (TMR) element, a superconductivity quantum interference device (SQUID), etc. can be employed. The determining technique can be any one of such conventional techniques as the magnetic susceptibility determination, the magnetic relaxation determination technique, etc. It is preferred to employ a GMR sensor (which is a magnetic resistance element) such as one disclosed in S. X Wang et al.'s "Biosensors and Bioelectronics, 201 o, Vol. 25, No. 9, p. 2051-2057", etc. For instance, it is possible to arrange such that magnetization of magnetic particle is detected with utilizing of a resistance value of the magnetic sensor which varies in association with variation of the magnetic field. Due to presence of an external magnetic field, the magnetic particle on the sensor is magnetized and the magnetized magnetic particle induces a change in the resistivity of the magnetic sensor. And, by converting such magnetic sensor resistivity into an electric signal and detecting this signal, the presence of the magnetic particle can be detected. Incidentally, the magnetic sensor per se can be formed as a chip.

In case a magnetic sensor is used in the measurement of the intensity of the signal derived from the detection antibody, the shape of the sensor element is not particularly limited, but can be a shape of e.g. a flat plate, a sphere, a cubic shape such as a cube, etc. For instance, it can be formed as a flat-plate like shape having material forming the sensor element laminated flatly thereon. The material constituting the sensor element is not limited to the below. Though not wishing in any way to be limited thereto, silicon or silica, inorganic compound such as titanium oxide, synthetic polymer such as acrylamide, polystyrene, polycarbonate can be used in forming a substrate, on which an antiferromagnetic layer containing PtMn, NiMn, IrMn, PdMn, PdPtMn, RhMn, etc. as the principal component thereof, a non-magnetic layer containing Ta, Ru, Cr, Rh, Ir, Au, Ag, Cu, Zr, Pt, Mo, W, etc. as the principal component thereof, a ferromagnetic layer containing NiFe, Co, CoFe, or the like as a principal component, a seed layer, an insulator layer, etc. can be placed in stack thereon, such materials can be selected appropriately in accordance with the detection method of electric signal.

The magnetic sensor, preferably, comprises a plurality of sensor elements to be capable of measuring a plurality of samples at one time. Each magnetic sensor element can be disposed accurately at a predetermined position on the substrate such as a chip or in the form of an array, be able to detect a magnetic signal independently. In this way, sensor will be configured to be usable in simultaneous measurement of reaction solutions comprising the biological sample required for the autoantibody quantification method of this disclosure added with different known amounts of competition antibody as well as the multiplexed simultaneous analysis for simultaneous measurement of a plurality of autoantibodies.

(iv) Step of Calculating Autoantibody Amount.

In the autoantibody quantifying method of this disclosure, the step (iv) is provided for calculating an amount of the autoantibody contained in the biological sample by utilizing, as an index therefor, an amount of the competition antibody that provides 50% reduction of the signal derived from the detection antibody which is bound to the autoantibody in absence of the competition antibody. Since the competition antibody is added by a known amount to the biological sample containing an autoantibody as a test substance, from comparison with such known amount of competition antibody, the amount of autoantibody contained in the biological sample is calculated.

In accordance with increase/decrease of the competition antibody amount added to the biological sample, the intensity of the signal derived from the detection antibody varies. If the amount of competition antibody added to the biological sample is large, because the competition antibody and the autoantibody compete with each other in bonding thereof to the antigen, the amount of competition antibody bound to the antigen will increase, whereas the amount of autoantibody bound to the antigen will decrease. Since the detection antibody does not recognize the competition antibody, but recognizes only the autoantibody, with decrease in the ratio of the autoantibody bound to the antigen, the intensity of the signal derived from the detection antibody will be reduced. Conversely, if the amount of competition antibody added to the biological sample is small, the amount of competition antibody bound to the antigen will decrease, whereas the amount of autoantibody bound to the antigen will increase, so that the intensity of the signal derived from the detection antibody will be increased. Accordingly, in association with increase of the competition antibody amount, the determined signal intensity per se will be reduced. Conversely, in association with decrease of the competition antibody amount, the determined signal intensity will be enhanced.

At the step of calculating the autoantibody amount, there is obtained a competition antibody amount which exhibits 50% reduction of the effect (this may be referred to as "$IC_{50}$" hereinafter) when the competition antibody competitively inhibits binding of the antigen with the autoantibody. Preferably, a calibration curve comprised of plotting of a relation between the amount of competition antibody added to the biological sample and the measured signal intensity is produced and based on such calibration curve, the $IC_{50}$ can be obtained. Preferably, $IC_{50}$ is calculated, with using a signal intensity measured in the absence of the competition antibody being 100%.

The $IC_{50}$ value can be considered as an amount of the autoantibody bonded to the antigen, assuming that the affinities for antigen of the autoantibody as the test substance and the competition antibody are equal to each other. As 50% of the autoantibody of the autoantibody contained in the biological sample is bonded to the antigen, it is understood that the biological sample as a whole contained the twice amount of autoantibody. With this, the amount of the autoantibody contained in the biological sample can be calculated as an absolute value.

In the measurement, if dilution or the like was effected on the biological sample, the amount of the autoantibody contained in the biological sample can be obtained with correction by multiplication of the dilution degree. Further, in case a reaction solution prepared with addition of a competition antibody solution to the biological sample is used at the step of reaction with the competition antibody, the amount of the autoantibody contained in the biological sample can be obtained with correction by multiplication of the mixing degree of the reaction solution preparation. In this, the mixing degree of the reaction solution can be obtained as follows.

mixing degree of the reaction solution=(reaction solution amount (biological sample+competition antibody solution))/(biological sample amount)

When the affinities for antigen of the autoantibody as the test substance and the competition antibody are not equal to each other, the amount of the autoantibody contained in the biological sample can be obtained with correction by multiplication of the affinity degree. The affinity degree can be obtained as follows, for example.

affinity degree=(affinity of autoantibody ($K_d$ value))/ (affinity of competition antibody ($K_d$ value))

(Autoantibody Quantifying Method Using Solid Phase Technique)

In the autoantibody quantifying method of this disclosure, the solid phase technique can be used particularly preferably. Next, an embodiment of the autoantibody quantifying method using such solid phase technique will be described in details with reference to FIGS. 1 and 2.

FIG. 1 shows that as a test substance 3, there is employed a human autoantibody for angiopoietin-like protein 3 (ANGPTL3) contained in a biological sample. As a solid support 1, a magnetic sensor element is employed, on which there was immobilized in advance ANGPTL3 as an antigen 2 which is specifically recognized and bound by the autoantibody as the test substance 3. The solid support 1 can have its surface modified for stable immobilization of the protein on its surface. To the biological sample, a known amount (concentration) of competition antibody 4 is added and mixed, and this mixture is used as a reaction solution. As the competition antibody 4, a sheep-derived anti-human ANGPTL3 is employed, and this is added in various amounts to the reaction solution.

Next, the reaction solution is reacted with the reaction surface of the solid support 1 on which the antigen 2 is immobilized. In this, the autoantibody as the test substance 3 in the biological sample and the competition antibody 4 bind competitively to the antigen 2. After the reaction, the reaction surface of the solid support 1 is washed with an appropriate aqueous solution such as water, physiological saline solution, various buffer solutions, etc., whereby the autoantibody as the test substance 3 and the competition antibody 4 non-reacted with the antigen 2 can be removed.

Next, the reaction surface of the solid support 1 is reacted with a detection antibody 5 that recognizes the autoantibody as the test substance 3, but does not recognize the competition antibody 4. The detection antibody 5 recognizes and binds only the autoantibody as the test substance 3 bound to the antigen 2. Here, as the detection antibody 5, a biotin 5b labelled anti-human IgG antibody 5a (rabbit-derived anti-human IgG antibody, sheep-derived anti-human IgG antibody, or goat-derived anti-human IgG antibody) was used. After the reaction, the reaction surface of the solid support 1 is washed with an appropriate aqueous solution such as water, physiological saline solution, various buffer solutions, etc., whereby the detection antibody 5 non-reacted with the test substance 3 is removed.

Subsequently, a labeling material 6 that captures the detection antibody 5 is added to the reaction surface of the solid support 1, thereby to label the detection antibody 5 and a label signal is measured. With this, the test substance 3 bound to the antigen 2 is labeled via the detection antibody 5 and a signal derived from this test substance 3 bound to the antigen 2 can be detected, and the intensity of this signal is in direct proportion to the amount of the test substance 3 bound to the antigen 2. Here, as the labeling material 6, there is employed an anti-biotin antibody 6a immobilized magnetic bead 6b is employed and a magnetic signal from this magnetic bead is measured by the magnetic sensor.

Figure 2:
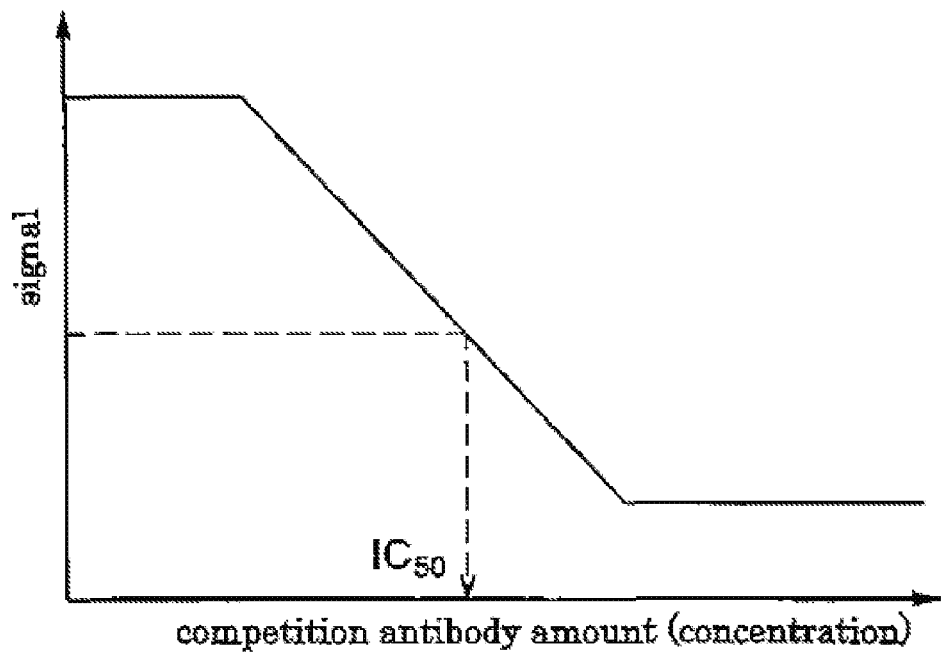
FIG. 2 is a graph showing one mode of $IC_{50}$ value calculation in the autoantibody quantification method relating to this disclosure.

Next, with using, as an index, the $IC_{50}$ value obtained from the relation between the measured signal intensity and the added competition antibody 4 amount, an amount (concentration) of the autoantibody as the test substance 3 is calculated. This calculation of autoantibody amount can be carried out as described above. As shown in FIG. 2, a calibration curve plotting the relation between the amount of competition antibody 4 added to the biological sample and the measured signal intensity is produced and based on such calibration curve, the amount of autoantibody contained in the biological sample can be quantified easily.

By binding the antigen to the solid support 1, strict separation is made possible between the autoantibody and the competition antibody 4 that were bound to the antigen 2 and the autoantibody and the competition antibody 4 that were not reacted with the antigen 2, so that the reliability of the absolute amount of the autoantibody contained in the biological sample is further enhanced. And, such separation too can be carried out by a simple operation such as washing of the solid support described above.

With this disclosure, it is possible to provide a method of quantifying an absolute amount of autoantibody contained in a biological sample easily. With the conventional methods, emphasis would be placed on either one of the readiness and quantification in the determination of an amount of autoantibody contained in a biological sample and it was difficult to configure a determination system having both of the above. As it was difficult to purchase or obtain high-purity standard substance of autoantibody, in particular human autoantibody. Therefore, if emphasis is placed on the quantification, there arises need for preparing calibration curve with using e.g. purified autoantibody as the standard substance. However, purification of autoantibody requires a complex and troublesome operation as well as much cost. In particular, such methods are not suitable for multiplexed simultaneous analysis that requires many different kinds of standard substance. On the other hand, if emphasis is placed on the readiness, for instance, a calibration curve would be produced with using a readily available patient specimen as a standard substance, for the purpose of autoantibody amount determination, or, such calibration curve was not produced and determination of autoantibody as a test substance would be made based on e.g. a value obtained by subtracting a blind test value from an actually determined value. But, such method was merely sub-quantitative method. Further, in the competition technique as one of the conventional antibody determination methods, determination of presence and amount of antibody contained in a biological sample is made based on a ratio of inhibition of 'binding by labeled competition antibody by the antibody contained in a biological substance relative to an antigen immobilized on an appropriate substrate. However, in the conventional method, the amount of antibody contained in a biological sample is determined by comparison with a calibration curve produced by varying a known amount of non-labeled antibody. Thus, as it is difficult to purchase or obtain a high-purity standard substance of autoantibody, such method does not solve the above-described drawbacks.

The autoantibody quantifying method of this disclosure is same as the conventional method in the respect of using a biological sample of a patient specimen as a standard substance. A competition antibody is added in various known amounts (concentrations) to a biological sample, thereby to cause competition between the autoantibody and the competition antibody for binding to the antigen. Then, a signal derived from the autoantibody is measured via a detection antibody that is not bound to the competition antibody, but bound only to the autoantibody. The intensity of the signal varies in accordance with variation of the added competition antibody amount. Then, using, as an index, an amount of competition antibody that results in 50% reduction in the intensity of the signal derived from the autoantibody in the absence of the competition antibody, the amount (concentration) of autoantibody contained in the biological sample is calculated. In particular, when it is possible to assume that the affinities of the autoantibody and the competition antibody for an antigen are equal, the amount of competition antibody resulting in 50% reduction in the intensity of the signal derived from the autoantibody can be considered as being equal to a half amount of autoantibody contained in the biological sample. Therefore, with this disclosure, it is possible to quantify an absolute amount of autoantibody contained in a biological sample even though using a readily available biological sample such as a patient specimen as the standard substance and this method is superior in its economic aspect as it does not require any complicated operation or costly reagent or the like. Further, as the amount of autoantibody contained in a biological sample can be determined as an absolute amount, a calibration curve concentration can be determined with using the biological sample as the standard substance, so it is also possible to provide an inexpensive and superior quantification standard substance for quantification of autoantibody. The autoantibody quantifying method according to this disclosure having both quantification and readiness can be expected to be useful for a multiplexed simultaneous analysis of autoantibody for which there is an increasing demand in recent years. Further, with the conventional methods, if determination is made with using different lots of reagent for a same biological sample, there tends to occur inter-lot error of variation of measured values as described above and this will be significantly problematic in the case of implementation in a commercial scale. On the other hand, with this disclosure, even when such inter-lot error of reagent occurs, since the calibration curve concentration can be determined as an absolute value, there is achieved the advantage of ability to obtain highly reliable result stably.

EXAMPLES

Next, the autoantibody quantifying method according to this disclosure will be explained in details. It is understood however that the autoantibody quantifying method according to this disclosure is not limited to these examples. Therefore, although an example of measuring angiopoietin-like protein (may be referred to as "ANGPTL3" hereinafter) as a test substance with using a GMR sensor, the autoantibody quantifying method according to this disclosure can be applied similarly also to other autoantibodies or other measuring methods.

(Example 1) Preparation of Printed Circuit Board Needed for Determination

1. Overview

In the following example, an amount of autoantibody in a biological sample was measured by a GMR sensor. In this example, the surface of the GMR sensor used in the measurement was subjected to a surface modification for protein immobilization.

2. Procedure

A printed circuit board (PCB) mounting eight (8) GMR sensors thereon was prepared and this was used in a measurement of autoantibody amount in the following example. The eight consecutive GMR sensors were mounted in a line with a fixed spacing there between. More particularly, the eight consecutive GMR sensors were disposed in parallel with each other with longitudinal alignment of a few mm or cm pitch to be able to correspond to respective wells in eight rows in a layout of 12 rows×8 columns. And, antigen immobilizing portions of the GMR sensors were mounted on the PCB in such a manner as to protrude therefrom or have protrusions corresponding to the respective wells in the eight columns of the well plate and the antigen immobilizing portions of the GMR sensors are attached to the leading end portions of these protrusions.

In order to immobilize protein on the GMR sensor surface, a following treatment was effected. Using a plasma cleaning device (G-1 000) from YES (Yield Engineering Corporation), cleaning operation of the PCB board was effected for 300 seconds under environment of 0.1 Torr/room temperature. Next, using a vacuum evaporation device (1224P) from YES corporation, on the PCB board, 3-aminopropyltriethoxysilane (Sigma, 440140) was vapor-deposited for 60 minutes under the environment of 0.5 Torr/150° C. Subsequently, under environment of normal pressure 150° C., the board was kept still for 16 hours under the environment of normal pressure/150° C. The PCB board after completion of these steps was returned to the room temperature and stored in a clean room until use.

(Example 2) Immobilization of Antigen Solution on GMR Sensor Surface

1. Overview

In the following example, on the GMR sensors on the PCB board after the surface modification treatment in Example 1, an antigen for the autoantibody as a test substance was immobilized.

2. Procedure

On 1 sensor of the PCB board after the surface modification treatment in Example 1, a human ANGPTL3 antigen (0.05 mg/ml: manufactured by R&D Systems Corporation) was dripped (dripping amount: 650 pl), with using a small amount liquid application device from Scienion Corporation. After dripping, the antigen was reacted for 1 hour for immobilization and the board was dipped for one hour at the room temperature in a blocking solution (1% block ace/

4.4% BSA) for the purpose of suppressing nonspecific bonding. After the dipping, the sensor was dried and kept still overnight at 4° C.

(Example 3) Searches for Competition Antibody and Detection Antibody

1. Overview

In this example, searches for a competition antibody and a detection antibody for use in measurement of an autoantibody were conducted. Here, a competition antibody is an antibody that competes with an autoantibody as a test substance for binding to an epitope on a same antigen. The autoantibody is determined with utilization of such competition reaction of the autoantibody and the competition antibody in competition for the antigen. A detection antibody is an antibody that binds to the autoantibody as a test substance, thus detecting presence of the test substance contained in a biological sample.

2. Procedure

As a prerequisite for competition reaction, it is essential that the competition antibody and the detection antibody not react with each other. For this reason, before a measurement test was actually conducted, it was confirmed that the competition antibody and the detection antibody did not react with each other (absence of cross-reactivity there between).

As competition antibodies, three kinds of antibody, i.e. a mouse-derived anti-human ANGPTL3 antibody (R&D Systems Corporation, MAB3829), a rat-derived anti-human ANGPTL3 antibody (R&D Systems Corporation, MAB38291), and a sheep-derived anti-human ANGPTL3 antibody (R&D Systems Corporation, AF3929), were purchased and used. More particularly, the mouse-derived ANGPTL3 antibody was obtained from a monoclonal mouse $IgG_{2B}$ clone #370207, with using *S. frugiperda* insect ovarian cell line Sf 21-derived recombinant human ANGPTL 3 (UniProtKB/Swiss-Prot Q9Y6C1: Ser17-Glu460) as an immunogen and was purified from a culture suspension liquid of hybridoma cell with proteins A and G. The rat-derived ANGPTL3 antibody was obtained from mouse $IgG_{2A}$ clone #370207, similarly to the mouse-derived ANGPTL3 antibody, except for using Ile19-Glu460 as an immunogen. The sheep-derived anti-human ANGPTL3 antibody was a polyclonal antibody obtained by immunizing a sheep with using the same immunogen as used in the mouse-derived ANGPTL3 antibody.

As detection antibodies, four kinds of antibody, i.e. a rabbit-derived anti-human IgG antibody/biotin-labeled (ROCKLAND Corporation, 609-4603), a rabbit-derived anti-human IgG antibody/biotin-labeled (ROCKLAND Corporation, 5 609-4612); a sheep-derived anti-human IgG antibody/biotin-labeled (ROCKLAND Corporation, 609-6602), and a goat (ziege)-derived anti-human IgG antibody/biotin-labeled (VECTOR Corporation, BA-3000), were purchased and used. More particularly, the rabbit-derived anti-human IgG antibody (ROCKLAND Corporation, 609-4603) was a polyclonal antibody obtained by repeated immunization of a rabbit with human IgG F(c) fragment. The rabbit-derived anti-human IgG antibody (ROCKLAND Corporation, 609-4612) was a polyclonal antibody using human IgG gamma heavy chain as an immunogen. The sheep-derived anti-human IgG antibody was a polyclonal antibody for human IgG (H+L) using human IgG whole molecule as an immunogen and was prepared by the immunoaffinity chromatography of single specificity antiserum isolated from an immunized animal with using human IgG binding agarose bead. The goat-derived anti-human IgG antibody was also a polyclonal antibody for the human IgG (H+L).

The specific procedure will be described next.

The competition antibody was prepared as 2 μg/ml solution with using dilution solution (1% BSA/PBS) and the detection antibody was prepared as 0.7 μg/ml solution with using dilution solution (1% BSA/PBS). And, anti-biotin antibody immobilization magnetic bead (Miltenyi Corporation, 150-106-0877) for detection was diluted 20 folds with dilution solution (1% BSA/PBS), thus respective solutions thereof were prepared.

The following solutions were added each by 0.5 ml to a 96 well plate of 12 rows×8 columns. Then, this well plate was mounted to an automatic reaction device self-developed by the applicant and the PCB boards prepared in Example 1 and Example 2 were also mounted to the automatic reaction device. Next antigen-antibody reactions were effected under a stirring rate and a reaction period identified below. Incidentally, the reactions were conducted at the room temperature. The automatic reaction device was driven such that the GMR sensors mounted on the PCT board moved from the first row to the twelfth row of the 96 well plate and the antigen immobilizing portions of the GMR sensors dipped in the solution added to the wells of the respective rows one after another. Although the automatic reaction device was used in this example, the operation may be effected manually also.

The solutions, stirring rates and reaction periods applied to the wells of the respective rows are summarized as follows.

$1^{st}$ and $2^{nd}$ rows: washing solution (PBST), stirring rate 1 Hz, reaction period 1 minute
$3^{rd}$ row: empty
$4^{th}$ row: competition antibody solution, stirring rate 1 Hz, reaction period 90 minutes
$5^{th}$, $6^{th}$, $7^{th}$ rows: washing solution (PBST), stirring rate 1 Hz, reaction period 1 minute
$8^{th}$ row: empty
$9^{th}$ row: detection antibody, stirring rate 1 Hz, reaction period 60 minutes
$10^{th}$, $11^{th}$, $12^{th}$ rows: washing solution (PBST), stirring rate 1 Hz, reaction period 1 minute After the above reactions, the PCB board was dismounted from the automatic reaction device and then mounted to a GMR measuring device self-developed by this applicant. The following solutions were added by 0.4 ml to a well plate of 2 rows×8 columns. Then, this well plate was mounted to the automatic reaction device self-developed by the applicant. Then, reactions and determinations were effected under stirring rates and reaction periods identified below. Incidentally, the reactions and the determinations were conducted at the room temperature. The automatic reaction device was driven such that the GMR sensors mounted on the PCT board moved from the first row to the second row of the 2 rows×8 columns well plate and the antigen immobilizing portions of the GMR sensors dipped in the solution added to the wells of the respective rows one after another. By determining change amounts of resistance values resulting from binding of the magnetic bead to the sensor surface at the second row, the amounts were detected as signals.

The solutions, stirring rates and reaction periods applied to the wells of the respective rows are summarized as follows.

Figure 3:
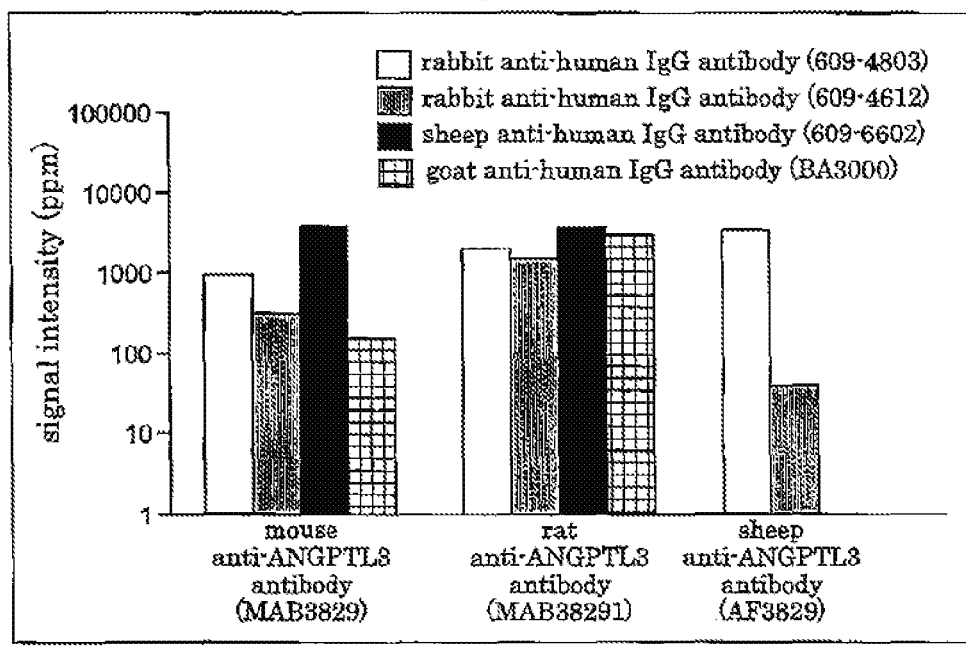
FIG. 3 is a graph showing results of Example 3 considering cross-reactivity between a competition antibody and a detection antibody.

$1^{st}$ row: washing solution (PBST), stirring rate 1 Hz, reaction period 3 minutes
$2^{nd}$ row: anti-biotin antibody immobilizing magnetic bead, stirring rate 1 Hz, reaction period 20 minutes 3. Results The results are shown in FIG. 3 and Table 1. From these results, it was confirmed that the combination of the sheep-derived anti-human ANGPTL3 antibody (R&D System Corporation, AF3829) as a competition antibody and the rabbit-derived anti-human IgG antibody/biotin-labeled (ROCKLAND Corporation, 609-4612) as a detection antigen and the combination of the sheep-derived anti-human ANGPTL3 antibody (R&D System Corporation, 609-6602) as a competition antibody and the goat-derived anti-human IgG antibody/biotin-labeled (VECTOR Corporation, BA-3000) as a detection antigen had no cross-reactivity, respectively.

TABLE 1

|  |  | competition antibody | | |
| --- | --- | --- | --- | --- |
|  |  | mouse-derived anti-human ANGPTL3 antibody (MAB3829) | rabbit-derived anti-human ANGPTL3 antibody (MAB39291) | sheep-derived anti-human ANGPTL3 antibody (AF3829) |
| detection antibody | rabbit-derived anti-human IgG antibody (609-4603) | 954.8 | 1961.1 | 3345.6 |
|  | rabbit-derived anti-human IgG antibody (609-4612) | 313.6 | 1454.0 | 39.2 |
|  | sheep-derived anti-human IgG antibody (609-6602) | 3767.6 | 3989.8 | −15.9 |
|  | goat-derived anti-human IgG antibody (BA-3000) | 156.6 | 2857.0 | −5.4 |

(Example 4) Measurement of Autoantibody Amount in Biological Sample

1. Overview

As combinations of competition antibody and detection antibody having no cross-reactivity were confirmed in Example 3, in this example, determinations of autoantibody amounts in patient specimens were actually conducted, with using these combinations.

2. Procedure

As a patient specimen, plasma obtained from a patient was used and determination of anti-human ANGPL3 antibody amount contained in such patient specimen was conducted. More particularly, the patient specimen was diluted four folds with using dilution solution (1% BSA/PBS). As the competition antibody, the sheep-derived anti-human ANGPL3 antibody (R&D Systems Corporation AF3829) was prepared from 6.4 ng/ml to 100 µg/ml concentration with using a dilution solution (1% BSA/PBS). Then, the competition antibody 55 µl prepared as above was mixed with 495 µl of patient specimen to form a reaction solution, thus providing sample group of competition antibody having final concentrations from 0.64 ng/ml to 10 µg/ml. Incidentally, a sample added with the dilution solution (1% BSA/PBS) instead of the competition antibody was used as a competition antibody non-added sample (competition antibody concentration=0 sample). As detection antibodies, three kinds of antibody, i.e. the rabbit-derived anti-human IgG antibody/biotin-labeled (ROCKLAND Corporation, 609-4612), the sheep-derived anti-human IgG antibody/biotin-labeled (ROCKLAND Corporation. 609-6602) and the goat-derived anti-human IgG antibody (VECTOR Corporation, BA-3000) were prepared to a concentration of 0.7 µg/ml with using the dilution solution (1% BSA/PBS).

The solutions thus prepared were added by 0.5 ml respectively to the 96 well plate of 12 rows×8 columns, like Example 3; and then, reactions were carried out at the automatic reaction device and the analysis was effected by the GMR determination device.

(Results)

Figure 4:
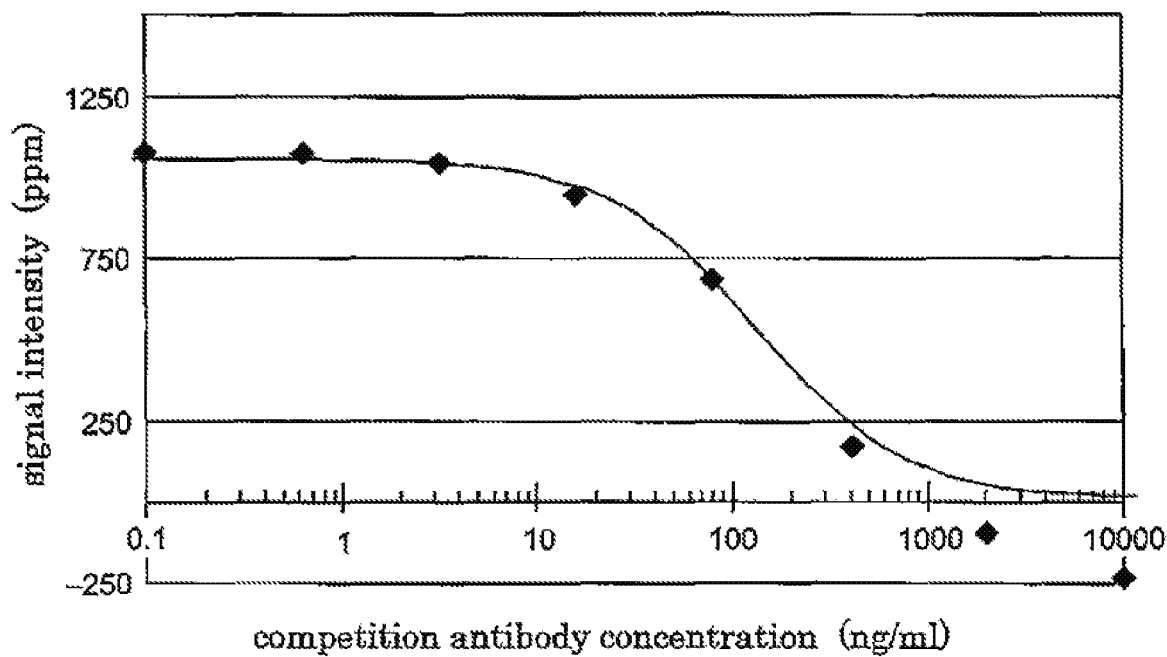
FIG. 4 is a graph showing a result in Example 4 in which determination was made on an anti-human ANGPTL antibody amount utilizing the autoantibody quantification method according to this disclosure, showing result using rabbit-derived anti-human IgG antibody as a detection antibody.
Figure 5:
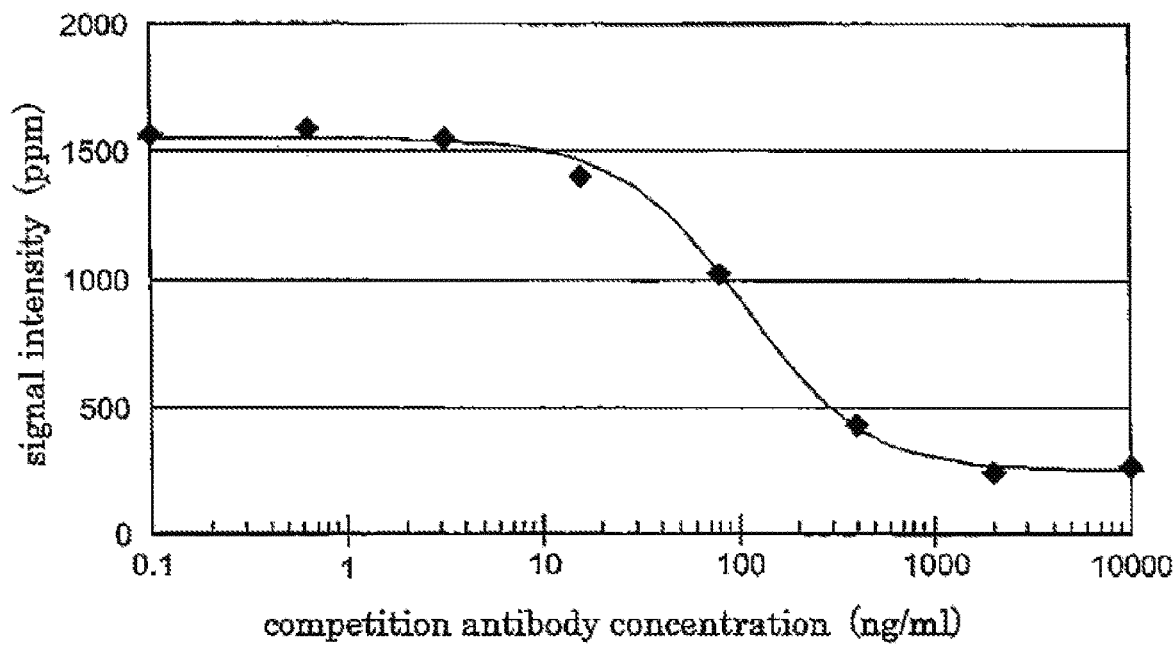
FIG. 5 is a graph showing a result in Example 4 in which determination was made on an anti-human ANGPTL antibody amount utilizing the autoantibody quantification method according to this disclosure, showing result using sheep-derived anti-human IgG antibody as a detection antibody.
Figure 6:
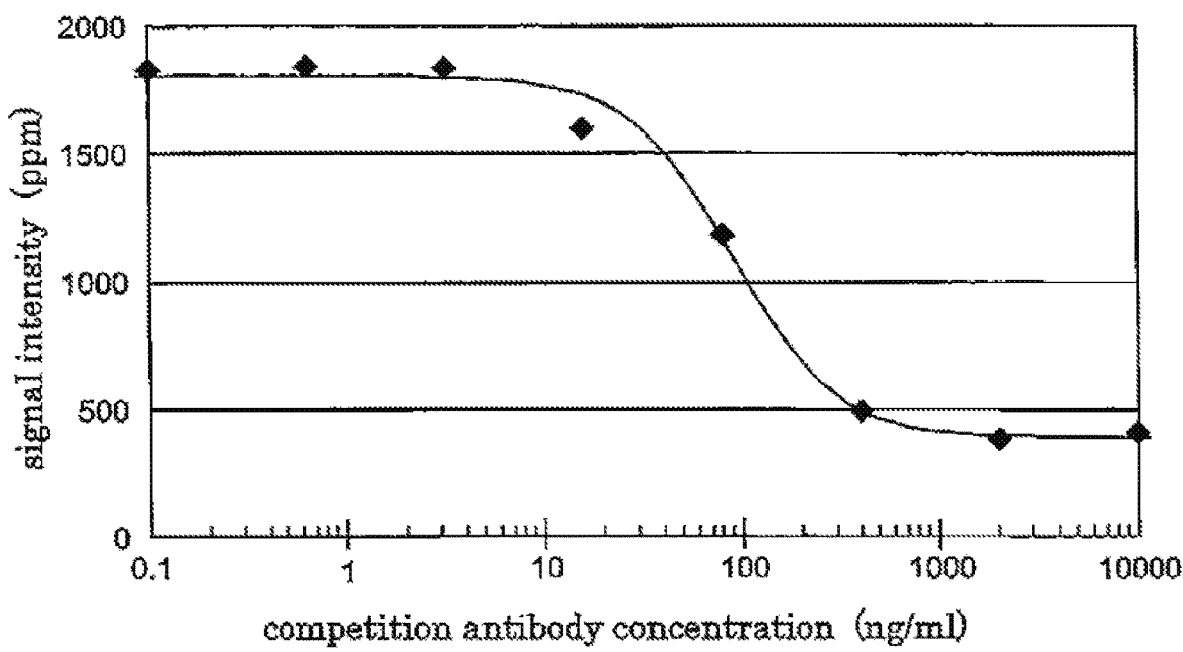
FIG. 6 is a graph showing a result in Example 4 in which determination was made on an anti-human ANGPTL antibody amount utilizing the autoantibody quantification method according to this disclosure, showing result using goat-derived anti-human IgG antibody as a detection antibody.

The results are shown in FIGS. 4 through 6. The results indicated that with whichever detection antibody used, signal reduction was observed with increase of the concentration of the competition antibody. An approximation formula was obtained from the test results and 50% inhibition concentrations ($IC_{50}$) were obtained. As the approximation formula, a 4-parameter logistic curve was obtained from Mathematical Formula 1 below and a calibration curve was obtained.

$$Y = d + \frac{(a-d)}{1 + \left(\frac{X}{c}\right)^b} \quad \text{[Mathematical Formula 1]}$$

In the Mathematical Formula 1, a=12.1, b=−1.15, c=134.0, d=1056 in case the rabbit-derived anti-human IgG antibody was used, a=246.81, b=−1.408, c=105.6, d=1548.6 in case the rabbit-derived anti-human IgG antibody was used, and a=388, b=−1.68, c=90.1, d=1803.1 in case the goat-derived anti-human IgG antibody was used, were substituted.

As the $IC_{50}$ values, $IC_{50}$=132.2 ng/ml was obtained when the rabbit-derived anti-human IgG antibody was used as the competition antibody (see FIG. 4); $IC_{50}$=137.0 ng/ml was obtained when the sheep-derived anti-human IgG antibody/biotin-labeled (ROCKLAND Corporation, 609-6602) was used as the competition antibody (see FIG. 5); and $IC_{50}$=122.8 ng/ml was obtained when the goat-derived anti-human IgG antibody/biotin-labeled (VECTOR Corporation, BA-3000) was used as the competition antibody (see FIG. 6).

Based on the above obtained $IC_{50}$ values, antibody concentrations were calculated from the following expression.

antibody concentration=$IC_{50}$×2×reaction solution preparation multiplying factor×dilution multiplying factor As an example, there will be shown the case of using the rabbit-derived anti-human IgG antibody (ROCKLAND Corporation, 609-4612). The obtained $IC_{50}$ was 132.3 ng/ml, for calibration of 50% to 100%, the value was multiplied by 2 (two). As for the reaction solution multiplying factor, since the reaction solution was prepared by adding 55 µl of competition antibody solution to 495 µl of patient specimen as the biological sample, a multiplying of (495+55)/495 is affected. And, with multiplication of 4 is effected since the dilution multiplying factor is 4, the concentration of autoantibody contained in the biological sample can be calculated. Namely, it can be calculated as 1175.1 ng/m, as the antibody concentration=132.2×2×550/495×4.

Similarly, when the autoantibody concentrations were calculated by using the results when using the sheep-derived anti-human IgG antibody/biotin-labeled and the goat-derived anti-human IgG antibody/biotin-labeled, the concentrations were calculated as 1217.4 ng/ml and 1091.6 ng/ml, respectively. Thus, with using whichever competition antibody, substantively same autoantibody concentrations could be obtained. Thus, it is understood that the autoantibody quantifying method of this disclosure has distinguished reliability and reproducibility.

In this way, with the autoantibody quantifying method according to this disclosure, in determination of an autoantibody contained as a test substance in a biological sample, through utilization of a competitive reaction with an antibody that competes with the autoantibody for binding to an antigen which is specifically recognized and bound by the autoantibody, the absolute amount (concentration) of the autoantibody contained in the biological sample can be quantified. With addition of a competition antibody by various known amounts (concentrations) to the biological sample, via a labeling detection antibody that does not bind to the competition antibody, but binds to the autoantibody, a labeling signal intensity derived from the autoantibody bound to the antigen is determined. In this, as the competition antibody is not detected, with increase of the competition antibody amount, the measured signal intensity decreases. Thus, the present inventors discovered that based on an amount of competition antibody that inhibits 50% of signal intensity by the competition antibody, an absolute amount of autoantibody contained in a biological sample can be determined easily.

Therefore, according to this disclosure, there can be provided a method of quantifying autoantibody that allows easy determination of an absolute amount of autoantibody contained in a biological sample. With the conventional methods, emphasis would be placed on either one of the readiness and quantification in the determination of an amount of autoantibody contained in a biological sample and it was difficult to configure a determination system having both of the above. On the other hand, according to this disclosure, although a readily available biological sample such as a patient specimen is used as a standard substance, an absolute amount of autoantibody contained in the biological sample can be quantified, and the method is superior in the respects of economy since it does not require any complicated operation or expensive reagent or the like. And, as the autoantibody amount in the biological sample can be determined as an absolute amount, a calibration curve concentration can be defined with using the biological sample as the standard substance. The autoantibody quantifying method of this disclosure having both the quantification ability and readiness as described above can be expected to prove useful in a multiplexed simultaneous analysis. Further, even when there is present inter-lot difference of reagent, as the calibration curve concentration can be formed as an absolute amount, highly reliable result can be obtained stably.

Therefore, the autoantibody quantifying method of this disclosure can be used in various fields that require quantification of autoantibody, in particular, in such industrial fields as medical treatment such as diagnosis, drug development and biological science, etc. For instance, the method can be used in quantification of autoantibody in diagnosis of autoimmune disease or a particular disease such as cancer, that is characterized by expression of the autoantibody, as well as in determination of a standard substance for production of calibration curve for the purpose of quantification of autoantibody.

In the foregoing embodiment, the following arrangements can be contemplated.

For example, in the embodiment described above, the antigen is immobilized on a solid support.

According to this disclosure, by causing an antigen to be bound to a solid support, strict separation is made possible between the autoantibody bound to the antigen and the competition antibody and between the autoantibody unreacted with the antigen and the competition antibody. Thus, the reliability of the measured value of the autoantibody amount is further enhanced. And, such separation too can be carried out by a simple operation such as washing of the solid support, so that the readiness can be further enhanced.

For instance, in the embodiment described above, the signal derived from the detection antibody is a magnetic signal.

With this disclosure, the magnetic signal can be detected with high sensitivity by e.g. a magnetic sensor or the like, so that an even more reliable determination result can be obtained stably in the quantification of the autoantibody contained in a biological sample.

The principles, preferred embodiment and mode of operation of the present invention have been described in the foregoing specification. However, the invention which is intended to protected is not to be construed as limited to the particular embodiments described above. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

DESCRIPTION OF REFERENCE MARKS/NUMERALS 1 solid support
2 antigen
3 test substance (autoantibody)
4 competition antibody
5 detection antibody
5a detection antibody molecule
5b biotin
6 labeling material
6a anti-biotin antibody molecule
6b magnetic bead

The invention claimed is:

1. A method of quantifying an autoantibody comprising the steps of:
  reacting a biological sample containing the autoantibody as a test substance with an antigen that is specifically recognized by and bound to the autoantibody, in competition with a known amount of a competition antibody that competes with the autoantibody for binding to the antigen;
  reacting the autoantibody bound to the antigen with a detection antibody that recognizes and binds to the autoantibody, but does not recognize the competition antibody;
  measuring a signal derived from the detection antibody bound to the autoantibody; and
  calculating an amount of the autoantibody contained in the biological sample by utilizing, as an index therefor, an amount of the competition antibody that provides 50% reduction of the signal derived from the detection antibody which is bound to the autoantibody in absence of the competition antibody.

2. The autoantibody quantifying method according to claim 1, wherein the antigen is fixed to a solid support.

3. The autoantibody quantifying method according to claim 1, wherein the detection antibody derived signal is a magnetic signal.

* * * * *